United States Patent [19]

Belko et al.

[11] Patent Number: 4,480,136
[45] Date of Patent: Oct. 30, 1984

[54] NORBORNYL OXYACETALDEHYDE, ORGANOLEPTIC USES THEREOF AND PROCESS FOR PREPARING SAME

[75] Inventors: Robert P. Belko, Woodbridge; Richard M. Boden, Ocean; Marie R. Hanna, Hazlet, all of N.J.

[73] Assignee: International Flavors & Fragrances Inc., New York, N.Y.

[21] Appl. No.: 456,984

[22] Filed: Jan. 10, 1983

Related U.S. Application Data

[60] Continuation-in-part of Ser. No. 357,157, Mar. 11, 1982, , which is a division of Ser. No. 303,012, Sep. 17, 1981, Pat. No. 4,354,043.

[51] Int. Cl.$^3$ .............................................. C07C 47/115
[52] U.S. Cl. ................................. 568/445; 252/522 R
[58] Field of Search ...................... 568/445, 432, 471; 252/552 R

[56] References Cited

U.S. PATENT DOCUMENTS

| | | | |
|---|---|---|---|
| 2,307,934 | 1/1943 | Loder et al. | 568/471 |
| 2,918,497 | 12/1959 | Walter et al. | 568/432 |
| 3,354,225 | 11/1967 | Kane | 568/665 |
| 3,636,113 | 1/1972 | Hall | 568/445 |
| 3,636,927 | 1/1972 | Baum | 568/665 |
| 4,053,657 | 1/1977 | Schreiber et al. | 252/522 R |
| 4,131,687 | 12/1978 | Mussinan et al. | 252/522 R |
| 4,254,043 | 10/1982 | Belko et al. | 568/445 |
| 4,391,744 | 7/1983 | Belko et al. | 252/522 R |
| 4,443,633 | 4/1984 | Boden et al. | 568/445 |

Primary Examiner—Werren B. Lone
Attorney, Agent, or Firm—Arthur L. Liberman

[57] ABSTRACT

Described is a compound having the structure:

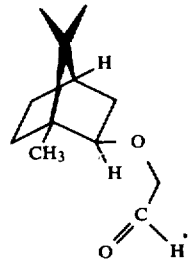

a norbornyl oxyacetaldehyde, prepared by oxidizing the norbornyl oxyethanol compound having the structure:

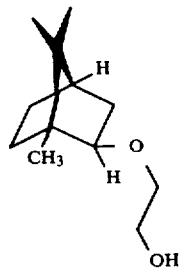

using air or oxygen and a silver or copper chromite catalyst; and organoleptic uses of such oxidation product in the field of perfumery, colognes and perfumed articles (e.g. perfumed plastics, solid or liquid anionic, cationic, nonionic or zwitterionic detergents, fabric softener compositions or drier-added fabric softener articles).

1 Claim, 5 Drawing Figures

FIG. 2

GLC PROFILE FOR EXAMPLE I

FIG. 1

GLC PROFILE FOR EXAMPLE I

FIG.5

NORBORNYL OXYACETALDEHYDE, ORGANOLEPTIC USES THEREOF AND PROCESS FOR PREPARING SAME

This application is a continuation-in-part of application for U.S. patent Ser. No. 357,157 filed on Mar. 11, 1982 which, in turn, is a divisional of application for U.S. patent Ser. No. 303,012 filed on Sept. 17, 1981, now U.S. Pat. No. 4,354,043 issued on Oct. 12, 1982.

BACKGROUND OF THE INVENTION

The instant invention relates to the compound which is a norbornyl oxyacetaldehyde having the structure:

Inexpensive chemical compounds which can provide intense and long-lasting woody, lavender-like, rosemary-like, green aroma with rosemary-like, lavandin-like, woody, natural pine oil and fresh herbaceous nuances on dry-out are desirable in the art of perfumery. Many of the natural materials which provide such fragrances and contribute such desired nuances to perfumery compositions are high in cost, unobtainable at time, vary in quality from one batch to another and/or are generally subject to the usual variations of natural products.

There is, accordingly, a continuing effort to find synthetic materials which will provide, enhance or augment the fragrance notes provided by natural essential oils or compositions thereof. Unfortunately, many of the synthetic materials either have the desired nuances only to a relatively small degree, or they contribute undesirable or unwanted odor to the compositions.

Although norbornyl derivatives are known in the art for producing piney aromas such as, for example, those disclosed in U.S. Pat. No. 4,153,811 issued on May 8, 1979, the inexpensive norbornyl oxyacetaldehyde type of compound has heretofore been unknown.

Thus U.S. Pat. No. 4,153,811 discloses the use of substituted norbornane derivatives of the genus of compounds having the structure:

wherein each of the dashed lines represents a carbon-carbon single bond or a carbon-carbon double bond with the proviso that at least one of the dashed lines is a carbon-carbon single bond; wherein n is 0 or 1 with the proviso that n is 1 when both dashed lines are carbon-carbon single bonds and n is 0 when one of the dashed lines is a carbon-carbon double bond; wherein $R_1$ and $R_2$ are each the same or different hydrogen or lower alkyl; wherein Y is:

wherein Z is one of the moieties:

wherein $R_3$ and $R_4$ are each alkyl; wherein $R_7$, $R_8$ and $R_{10}$ are each the same or different hydrogen or lower alkyl; wherein $R_9$ and $R_9'$ taken separately are the same or different lower alkyl, or taken together is lower alkylene; wherein the dotted line represents a carbon-carbon single bond or a carbon-carbon double bond; and wherein each of the wavy lines represents, in the alternative, exo or endo isomers.

U.S. Pat. No. 3,852,358 issued on Dec. 3, 1974 discloses a process for producing 2-acetyl-3,3-dimethyl-5-norbornene in both the exo and endo forms which have uses in perfumery and other fragrance applications. These compounds have the structures:

These compounds, produced by reaction of cyclopentadiene with mesityl oxide, are starting materials for producing a number of the compounds of our invention. However, the compounds of our invention have unexpected, unobvious and advantageous properties when compared with the 2-acetyl-3,3-dimethyl-5-norbornene of U.S. Pat. No. 3,852,358.

U.S. Pat. No. 3,942,761 discloses the use in perfumery of 4-(2'-norbornyl)-2-butanones having the structure:

wherein $R_1$ is hydrogen or methyl and R is hydrogen or lower alkyl containing from 1 to 8 carbon atoms. Such compounds have structures which are different in kind from the structures of the compounds of our invention. Also disclosed as intermediates for producing the foregoing compounds are compounds having the generic structure:

wherein the dotted line is a carbon-carbon single bond or a carbon-carbon double bond. In addition, the following reaction sequence is set forth therein:

Arctander, "Perfume and Flavor Chemicals", 1969, Vol. 1, discloses the use in perfume compositions and in foodstuff flavors of "fenchone", "fenchyl alcohol", "camphene carbinol", and "camphene carbinyl acetate", thus:

(i) "1385: FENCHONE laevo-Fenchone (dextro- is known but less common as a fragrance material). 1,3,3-trimethyl-2-norbornanone. 1,3,3-trimethyl bicyclo-1,2,2-heptanone-2.

Warm-camphoraceous, powerful and diffusive, basically sweet odor. Warm, somewhat burning and bitter taste with a medicinal note. This ketone finds some use as a masking odor in industrial fragrances. It is also used in the reconstruction of fennel oil and a few other essential oils. In spite of its rather unpleasant taste, it is used in various berry complex flavors, in spice complexes and in certain types of liquor flavoring. The concentration used is about 0.1 to 5 ppm in the finished product."

(ii) "1387: FENCHYL ALCOHOL 1,3,3-trimethyl-2-norbornanol. 1,3,3-trimethyl bicyclo-1,2,2-heptanol -2. 2-fenchanol. Fenchol.

The racemic alpha-fenchol has a somewhat lower melting point, and the beta-fenchols are all liquid at room temperature. Fenchol made by reduction of fenchone from cedarleaf oil is usually a mixture of several isomers, including the crystallne alpha-isomers. The beta-isomer forms a crystalline hydrate which may be sold at room temperature. Almost insoluble in water, soluble in alcohol, miscible with oils. Powerful and diffusive, camphor-like but sweeter and more citrus-like almost lime-like color with more or less of an earthy-dry character, according to the composition and isomer-ratio. The taste is somewhat bitter-lime-like, camphoraceous and slightly woody-musty. This interesting alcohol (or mixed alcohols) finds use in perfume compositions ranging from woody or herbaceous to citrus-lime and even certain floral types. It produces power and "lift" to floral fragrances, and solid background to lime and other citrus bases, having the advantage over the terpenes in being very stable in soap. Fenchyl alcohol is also used in flavor compositions such as strawberry and other berries, lime and spice, etc. The concentration is normally low, e.g. 0.2 up to 5 ppm in the finished product."

(iii) "1028: 3,3-DIMETHYL-$\Delta^2$, beta-NORBORNANE-2-ETHANOL. "Camphene carbinol".

Sweet, camphoraceous, warm and soft odor with a woody undertone. Upon standing it may develop an odor resembling that of celluloid.

Although rarely offered commercially, this chemical could find some use in perfume compositions of the woody, oriental and orissy type, in new variations of pine fragrances, and in various soap and detergent perfumes".

(iv) "1029: 3,3-DIMETHYL-$\Delta^2$-beta-NORBORNANE-2-ETHYLACETATE "Camphene carbinyl acetate".

Mild and sweet-woody odor with a floral-piney undertone. The commercial products are probably not well-defined single chemicals, and great variations in odor have been observed.

This ester has been developed in line with the research on sandalwood type odors. The parent alcohol "camphene carbinol" was once considered useful as a sandalwood type material, but it has found more use as a sweetening and enriching ingredient in sophisticated pine fragrances. The title ester finds limited use in perfume compositions of woody character, fougeres, pine fragrances, etc. and it blends very well with the cyclohexanol derivatives, ionones, isobornylacetate, nitromusks, etc.".

BRIEF DESCRIPTION OF THE DRAWINGS

showing the production of the norbornyl oxyacetaldehyde of our invention.

DETAILED DESCRIPTION OF THE DRAWINGS

Figure 1:
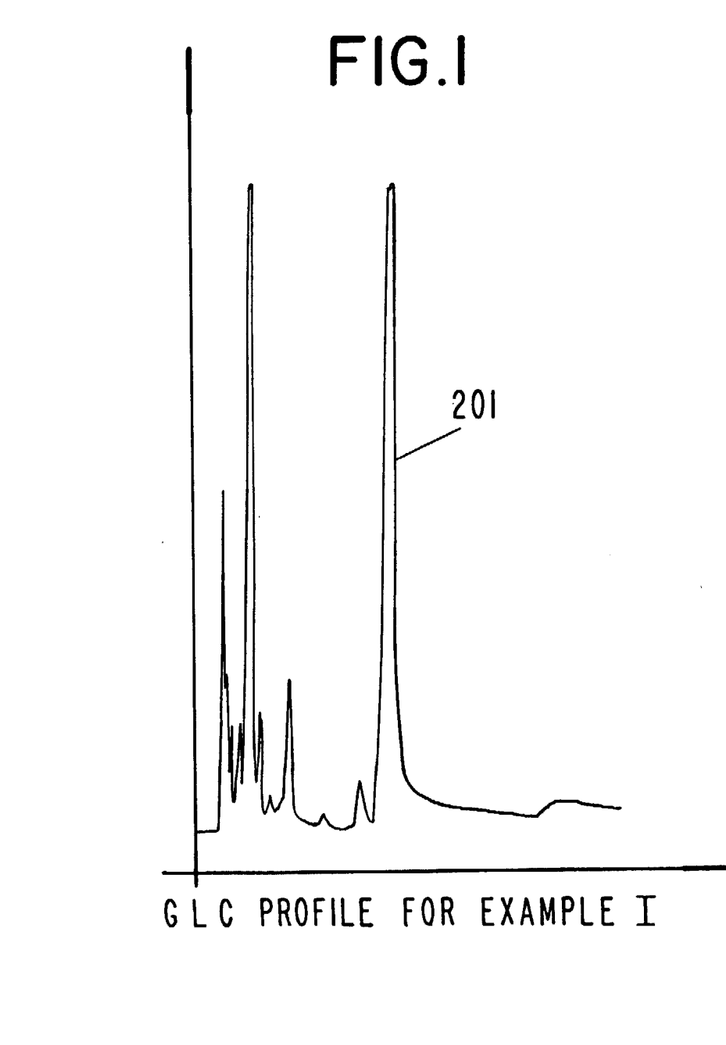
FIG. 1 is the GLC profile of the reaction product of Example I prior to distillation (conditions: 10'×¼" SE-30 column programmed at 160° C. isothermal).
Figure 2:
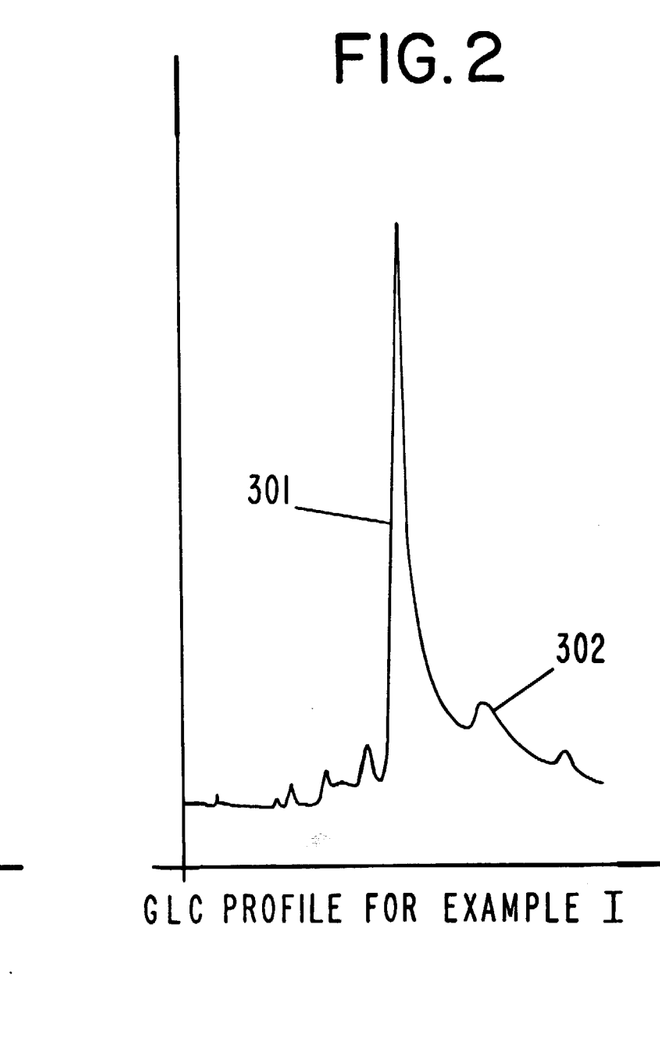
FIG. 2 is the GLC profile of the distillation product of the reaction product of Example I containing the compound having the structure.
Figure 5:
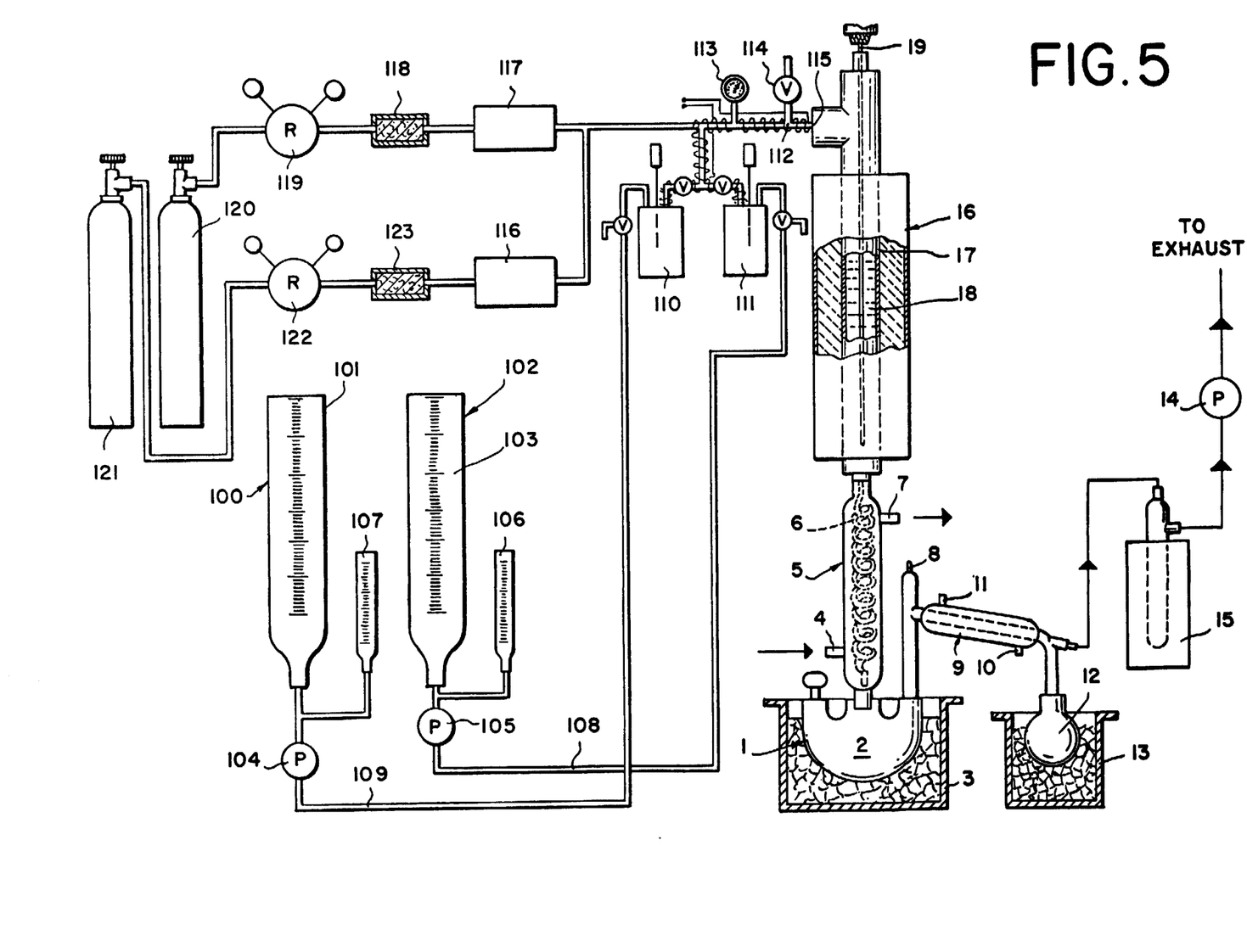
FIG. 5 is a schematic diagram of the apparatus used in order to carry out the oxidation reaction of Example I in order to effect the chemical reaction.

FIG. 1 is the GLC profile for the reaction product of Example I, the reaction carried out in the apparatus, the diagram for which is in FIG. 5. Peak 201 of the GLC profile contains the compound having the structure:

FIG. 2 is the GLC profile for the distillation product of the reaction product of Example I (conditions: 10'×¼" SE-30 column programmed at 160° C. isothermal). Peak 301 represents the compound having the structure:

Peak 302 represents the alcohol reactant having the structure:

FIG. 5 represents a schematic diagram of the process equipment for carrying out the process of Example I for effecting the reaction:

wherein the alcohol having the structure:

is oxidized over a silver catalyst to form the aldehyde having the structure:

Organic reactant feed 100 which is the alcohol having the structure:

held in holding tank 101 calibrated according to calibration apparatus 107 using pump 104 is fed through tube 109 simultaneously with water feed 103 held in holding tank 102 calibrated by calibration apparatus 106 (using pump 105 and tube 108 for the water feed) through vaporizers 110 (for the alcohol feed) and 111 (for the water feed) (wherein the mixture is heated) and then through heated tube 112 equipped with pressure gauge 113 and release value 114 into reaction tube 17 containing catalyst 18 (the reaction tube being heated using a cylindrical furnace 16 at 115). The catalyst bed 18 is rotated as a result of the rotation of rotatable rod 19. Simultaneously air held in pressurized cylinder 120 under pressure and nitrogen held in pressurized cylinder 121 uppumped through regulator 119 (for the air) and regulator 122 (for the nitrogen) and filter 118 (for the air) and filter 123 (for the nitrogen) using flow mass controller 117 (for the air) and mass flow controller 116 (for the nitrogen) into heated tube 112 thereby creating a mixture at 112 of air, nitrogen, alcohol having the structure:

and water vapor. The reaction mixture passes through catalyst bed 18 through condensation coil 6 which is cooled using cooling water entering the heat exchange 5 at location 4 and exiting at location 7. The condensed reaction product consisting essentially of the compound having the structure:

is retained in flask 2 at location 1, flask 2 being cooled using ice bath 3. Vacuum source 14 is used to assist the flow of the organic feed, the water feed, the nitrogen and the air or oxygen through reactor 17 into flask 2. Volatiles are condensed in flask 12 cooled by dry ice bath 13 and in the Dewar dry ice bath 15. Assisting in the cooling of the volatiles not retained in flask 2 is heat exchanger 9 wherein water is used as a coolant entering the heat exchanger at location 10 and existing from the heat exchanger at location 11.

THE INVENTION

The present invention provides the compound having the structure:

The compound of our invention produced according to the process of our invention is capable of augmenting, enhancing or providing woody, lavender-like, rosemary-like, green aroma with rosemary-like, lavandin-like, woody, natural pine oil and fresh herbaceous nuances on dry-out in perfume compositions, colognes and perfumed articles (e.g. perfume polymers, solid or liquid anionic, cationic, nonionic or zwitterionic detergents, fabric softener articles, drier-added fabric softener articles, fabric softener compositions, cosmetic powders, hair preparations, shampoos and the like).

The compound having the structure:

may be in either exo or endo form, that is, having the structures:

or this compound having the structure:

can represent mixtures of both compounds having the structures:

The compound of our invention is produced by first reacting the compound having the structure:

with oxygen or air according to the oxidation reaction:

-continued which is preferably carried out in apparatus described in the "Detailed Description of the Drawings" section of the instant specification, supra, and schematically shown in FIG. 5. The oxidation may use either air or oxygen. The oxidation catalyst may either be silver or copper chromite ($CuCrO_3$).

The reaction temperature may vary from 200° C. up to 500° C. but the temperature is dependent upon the desired yield and required residence time of the reactant compound having the structure:

in contact with the solid catalyst. Necessarily, the reaction is vapor phase and the surface area of catalyst and flow rate of reactant as well as residence time and reaction temperature and pressure are all important variables which must be optimized in relation to one another if yield and conversion of product are to be optimized. It is preferred that the reaction be carried out in the presence of water vapor and it is also preferred that the water flow rate and flow rate of alcohol reactant be approximately equal. The gas flow rates may vary between 50 and 400 ml per minute with a preferred oxygen flow rate of 285 ml per minute at a temperature of reaction of 450° C.; a liquid alcohol flow rate of 2 ml per minute and water flow rate of 2 ml per minute. As will be seen from an examination of FIG. 1 (the GLC profile of the reaction product of Example I) the yield using the foregoing conditions is approximately 50%. Separation of the aldehyde reaction product from the alcohol reactant and recycling of the alcohol reactant will, of course, raise the yield. A higher temperature of reaction, e.g. 500° C. and longer residence time (e.g. greater distance of travel of reactant through catalyst and/or area of contact with catalyst) will raise the yield to approximately 80%, the higher residence time being approximately 20% greater than what is used in Example I.

The aldehyde compound having the structure:

(hereinafter referred to as the norbornyl oxyacetaldehyde) prepared in accordance with the process of our invention and one or more auxiliary perfume ingredients including, for example, alcohols, aldehydes other than the norbornyl oxyacetaldehyde of our invention, ketones, terpenic hydrocarbons, nitriles, esters, lactones, natural essential oils and synthetic essential oils, may be admixed so that the combined odors of the individual components produce a pleasant and desired fragrance particularly and preferably in the pine and lavender fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all states of evaporation and substances which retard evaporation; and (d) top notes which are usually lowboiling, fresh-smelling materials.

In perfume compositions, it is the individual components which contribute their particular olfactory characteristics, however, the overall sensory effect of the perfume composition will be at least the sum total of the effects of each of the ingredients. Thus, the norbornyl oxyacetaldehyde composition of matter prepared in accordance with the process of our invention can be used to alter, modify or enhance the aroma characteristics of a perfume composition, for example, by utilizing or moderating the olfactory reaction contributed by another ingredient or other ingredients in the composition.

The amount of norbornyl oxyacetaldehyde prepared in accordance with the process of our invention which will be effective in perfume compositions as well as in perfumed articles (e.g. perfumed polymers, anionic, nonionic, cationic or zwitterionic detergents, soaps, fabric softener compositions, fabric softener articles and hair preparations) and colognes depends upon many factors including the other ingredients, their amounts and the effects which are desired. It has been found that perfume compositions containing as little as 0.01% of the norbornyl oxyacetaldehyde composition prepared in accordance with the process of our invention or even less (e.g. 0.005%) can be used to impart a lavender, woody and piney aroma with a fresh herbaceous background to soaps, cosmetics, anionic, cationic, nonionic or zwitterionic detergents, perfumed polymers, fabric softener compositions, fabric softener articles or other products. The amount employed can range up to 70% of the fragrance components and will depend on considerations of cost, nature of the end product, the effect desired on the finished product and the particular fragrance sought.

The norbornyl oxyacetaldehyde composition prepared in accordance with the process of our invention is useful (taken alone or taken together with other ingredients in perfume compositions) as an olfactory component in detergents and soaps, space odorants and deodorants, perfumes, colognes, toilet water, bath preparations such as creams, deodorants, hand lotions and sun screens; powders such as talcs, dusting powders, face powders, microporous "perfumed" slow release polymers, (e.g. polyurethane microporous polymers) and the like. When used as an olfactory component in perfumed articles, as little as 0.05% of the norbornyl oxyacetaldehyde prepared in accordance with the process of our invention will suffice to impart a woody, lavender, piney aroma with herbaceous nuances to pine or lavender formulations. Generally no more than 6% of the norbornyl oxyacetaldehyde composition of our invention based on the ultimate end product is required in the perfumed article.

In addition, the perfume composition or fragrance composition of our invention can contain a vehicle or carrier for the norbornyl oxyacetaldehyde composition prepared in accordance with the process of our invention. The vehicle can be a liquid, such as a non-toxic alcohol (e.g. ethyl alcohol), a non-toxic glycol (e.g. 1,2-propylene glycol) or the like. The carrier can also be an absorbent solid such as a gum (e.g. gum arabic or xanthan gum) or components for encapsulating the composition (such as gelatin) as by coacervation or polymers such as urea formaldehyde polymers.

It will thus be apparent that the norbornyl oxyacetaldehyde prepared in accordance with the process of our invention can be utilized to alter, modify or enhance sensory properties, particularly organoleptic properties such as fragrances of a wide variety of consumable materials.

The following Example I sets forth a means for synthesizing the norbornyl oxyacetaldehyde of our invention. The following Examples II and following serve to illustrate the organoleptic utilities of the norbornyl oxyacetaldehyde of our invention.

All parts and percentages given herein are by weight unless otherwise specified.

EXAMPLE I

PREPARATION OF NORBORNYL OXYACETALDEHYDE

Reaction:

Using the apparatus of FIG. 5, a catalytic oxidation of the alcohol having the structure:

is carried out. Maintaining the silver catalyst and reaction tube at a temperature of 450° C. (using furnace 16 and silver catalyst 18 on shaft 19 in reactor 17) oxygen held in vessel 120 is permitted to flow at a flow rate of 230 ml per minute through regulator 119, filter 118 and mass flow controller 117 through heater 112 while at the same time nitrogen at the flow rate of 100 ml per minute is permitted to flow through regulator 122, filter 123 and mass flow controller 116 whereupon the nitrogen flow joins the oxygen flow and the combined gasses are fed through heater 112 into reactor 17. Simultaneously, the alcohol having the structure:

held in holding tank 101 is pumped through pump 104 into vaporizer 110 through heating tube 112 along with the oxygen and nitrogen. Simultaneously, water 103 in holding tank 102 is pumped through pump 105 through tube 108 into vaporizer 111 and finally through heated tube 112 along with the oxygen, nitrogen and the alcohol reactant having the structure:

and finally into the reactor 17 through the silver catalyst 18 at 450° C. The flow rate of the alcohol having the structure:

is 2 ml per minute (liquid). The liquid flow rate of the water is also 2 ml per minute.

The reaction product having the structure:

is condensed in heat exchanger 5 at 6 and is collected at location 1 in flask 2 which is cooled by ice bath 3. Volatiles are collected in flask 12 and cooled by dry ice bath 13. A vacuum 14 is applied wherein the final volatiles are not permitted to escape but are collected at 15.

The detailed description of FIG. 5 is set forth in the Detailed Description of the Drawings for FIG. 5.

FIG. 1 is the GLC profile for the reaction product prior to distillation. Peak 201 is the peak for the compound having the structure:

(conditions: 10′ × ¼″ SE-30 column programmed at 160° C. isothermal).

FIG. 2 is the GLC profile for the distillation product, bulked fractions 5–10 of the distillation product of the reaction product above. The distillation is carried out on a 12″ stone packed column yielding the following fractions:

| Fraction Number | Vapor Temp. (°C.) | Liquid Temp. (°C.) | Pressure mm/Hg. | Reflux Ratio | Weight of Fraction (grams) |
|---|---|---|---|---|---|
| 1 | 24/40 | 24/85 | 1.2/1.2 | 9:1 | 18.3 |
| 2 | 60 | 113 | 1.2 | 9:1 | 2.0 |
| 3 | 67 | 114 | 1.2 | 9:1 | 6.5 |
| 4 | 80 | 114 | 1.2 | 9:1 | 5.1 |
| 5 | 80 | 114 | 1.2 | 9:1 | 6.4 |
| 6 | 80 | 114 | 1.2 | 9:1 | 11.9 |
| 7 | 80 | 114 | 1.2 | 2:1 | 6.6 |
| 8 | 82 | 115 | 1.2 | 2:1 | 9.2 |
| 9 | 82 | 115 | 1.0 | 2:1 | 6.8 |

-continued

| Fraction Number | Vapor Temp. (°C.) | Liquid Temp. (°C.) | Pressure mm/Hg. | Reflux Ratio | Weight of Fraction (grams) |
|---|---|---|---|---|---|
| 10 | 82 | 115 | 1.0 | 2:1 | 10.2 |
| 11 | 81 | 115 | 1.0 | 2:1 | 11.3 |
| 12 | 81 | 135 | 1.0 | 2:1 | 6.3 |
| 13 | 72 | 182 | 1.1 | 2:1 | 1.4 |

Figure 3:
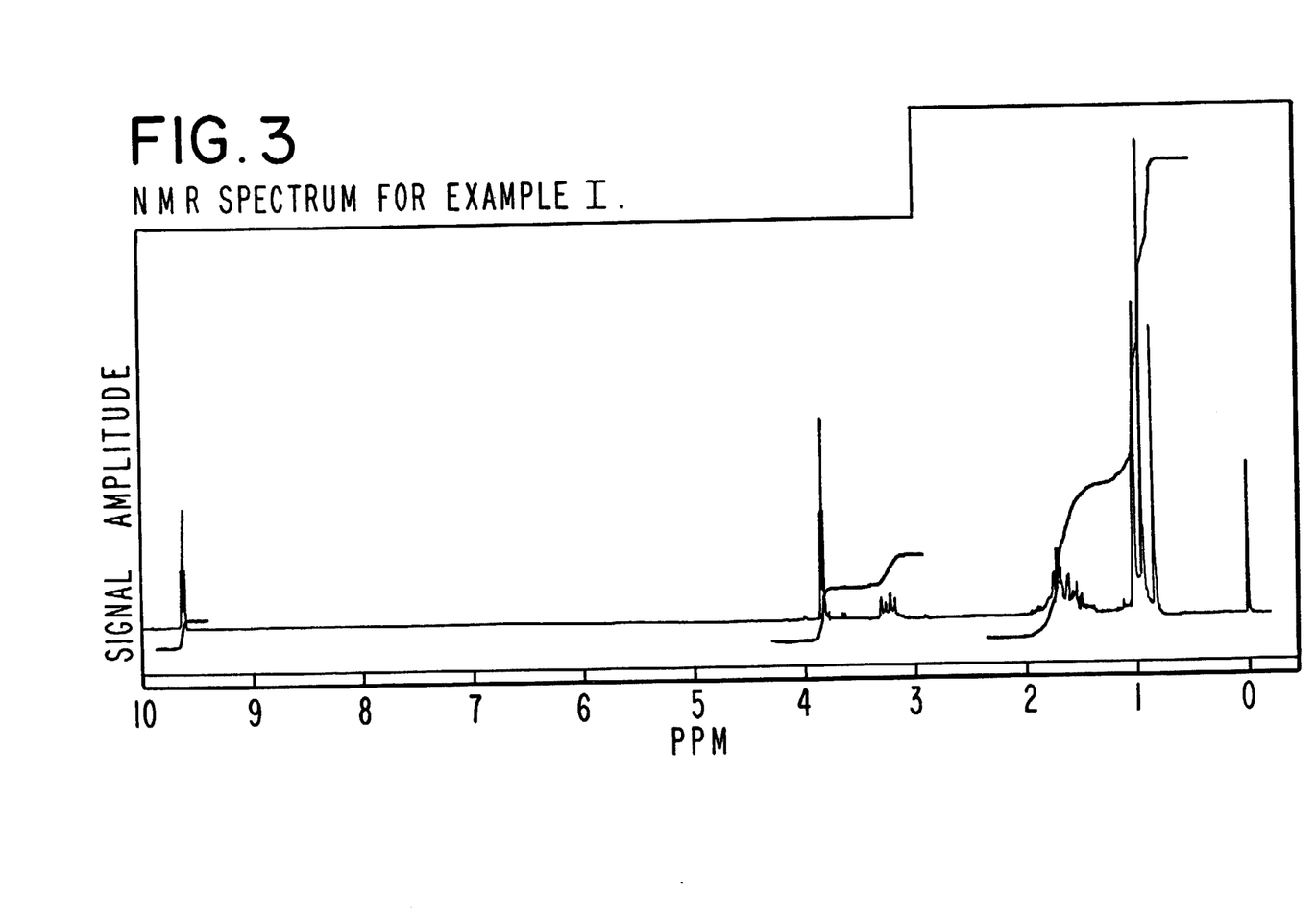
FIG. 3 is the NMR spectrum for the distillation product of Example I containing the compound having the structure.

FIG. 3 is the NMR spectrum for bulked fractions 5–10 of the foregoing distillation.

Figure 4:
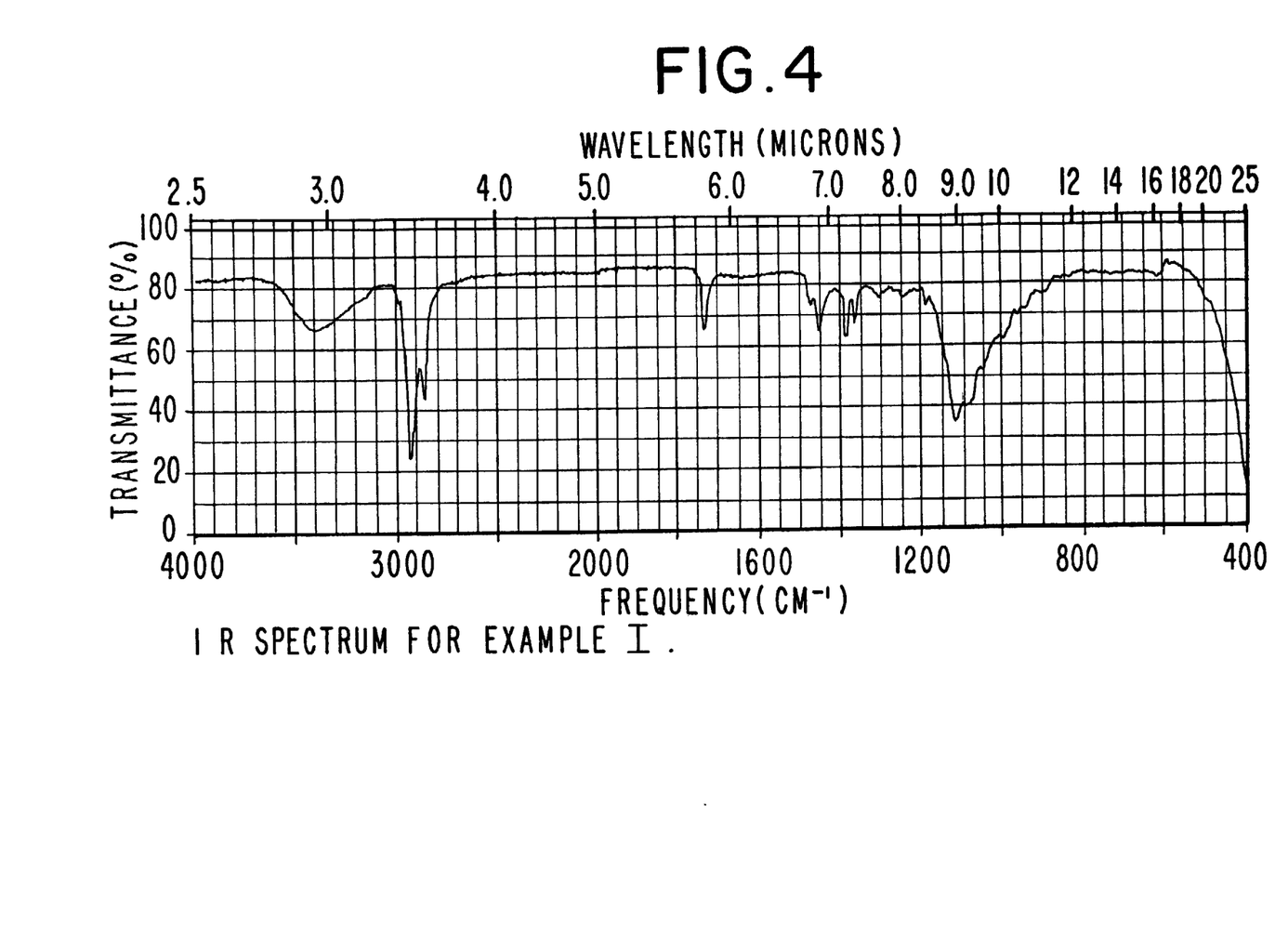
FIG. 4 is the infra-red spectrum for the distillation product of the reaction product of Example I containing the compound having the structure.

FIG. 4 is the infra-red spectrum for bulked fractions 5–10 of the foregoing distillation.

EXAMPLE II

PINE FRAGRANCE

The following pine fragrance formulation is prepared:

| Ingredients | Parts by Weight |
|---|---|
| Isobornyl acetate | 100 |
| Camphor | 10 |
| Terpineol | 25 |
| Fir balsam absolute (50% in diethyl phthalate) | 20 |
| Coumarin | 4 |
| Linalool | 30 |
| Fenchyl alcohol | 10 |
| Anethol | 12 |
| Lemon terpenes washed | 50 |
| Borneol | 5 |
| Galbanum oil | 5 |
| Turpentine Russian | 150 |
| Eucalyptol | 50 |
| 2,2,6-trimethyl-1-cyclohexene-1-carboxaldehyde | 12 |
| Maltol (1% in diethyl phthalate) | 5 |
| Bulked fractions 5–10 of the distillation product of Example I consisting of the compound having the structure: | 28 |

The norbornyl oxyacetaldehyde prepared according to Example I imparts to the pine formulation an intense lavender, woody, fresh herbaceous aroma profile. The pine formulation with the additional intense nuances caused by the use of the product of Example I, has advantageous and unexpected properties in the perfume industry.

EXAMPLE III

PREPARATION OF COSMETIC POWDER COMPOSITIONS

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
|---|---|
| The compound having the structure: (structure shown with CH₃, H, O, C, H, O, H atoms) (bulked fractions 5-10 of the distillation product of the reaction product of Example I). | A woody, lavender-like, rosemary-like, green aroma with rosemary-like, lavandin-like, woody, natural pine oil and fresh herbaceous nuances on dry-out. |
| Perfume composition produced according to Example II | A piney, lavender, woody and herbaceous aroma. |

EXAMPLE IV

PERFUMED LIQUID DETERGENTS

Concentrated liquid detergents (lysine salt of n-dodecylbenzene sulfonic acid as more specifically described in U.S. Pat. No. 3,948,818, issued on Apr. 6, 1976 incorporated by reference herein) with aroma nuances as set forth in Table I of Example III, are prepared containing 0.10%, 0.15%, 0.20%, 0.25%, 0.30% and 0.35% of the substance set forth in Table I of Example III. They are prepared by adding and homogeneously mixing the appropriate quantity of substance set forth in Table I of Example III in the liquid detergent. The detergents all possess excellent aromas as set forth in Table I of Example III, the intensity increasing with greater concentrations of substance as set forth in Table I of Example III.

EXAMPLE V

PREPARATION OF COLOGNES AND HANDKERCHIEF PERFUMES

Compositions as set forth in Table I of Example III are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example III are imparted to the colognes and to the handkerchief perfumes at all levels indicated.

EXAMPLE VI

PREPARATION OF SOAP COMPOSITIONS

One hundred grams of soap chips (per sample) (IVORY ®, produced by the Procter & Gamble Company of Cincinnati, Ohio), are each mixed with one gram samples of substances as set forth in Table I of Example III until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example III.

EXAMPLE VII

PREPARATION OF SOLID DETERGENT COMPOSITIONS

Detergents are prepared using the following ingredients according to Example I of Canadian Pat. No. 1,007,948 (incorporated herein by reference):

| Ingredient | Percent by Weight |
|---|---|
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table I of Example III. Each of the detergent samples has an excellent aroma as indicated in Table I of Example III.

EXAMPLE VIII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolvable" paper ("Dissolvo Paper")
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table I of Example III.

Fabric softening compositions prepared according to Example I at column 15 of U.S. Pat. No. 3,632,396 having aroma characteristics as set forth in Table I of Example III, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example III is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table I of Example III, supra.

EXAMPLE IX

HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example III, supra | 0.10 weight percent |

The perfuming substances as set forth in Table I of Example III add aroma characteristics as set forth in Table I of Example III which are rather intense and aesthetically pleasing to the users of the soft-feel, good-hold pump hair sprays.

EXAMPLE X

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat®755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting COMPOSITION A & COMPOSITION B are then mixed in a 50:50 wt ratio of A:B and cooled to 45° C. and 0.3 wt percent of perfuming substance as set forth in Table I of Example III is added to the mixture. The resulting mixture is cooled to 40° C. and blending is carried out for an additional one hour in each case. At the end of this blending period, the resulting material has a pleasant fragrance as indicated in Table I of Example III.

PATENTS INCORPORATED HEREIN BY REFERENCE

The following patents referred to supra are hereby incorporated herein by reference:
U.S. Pat. No. 3,632,396
U.S. Pat. No. 3,948,818
Canadian Pat. No. 1,007,948

What is claimed is:

1. The norbornyl oxyacetaldehyde having the structure:

* * * * *